US00PP13428P2

(12) United States Plant Patent
Mislow, III

(10) Patent No.: US PP13,428 P2
(45) Date of Patent: Dec. 31, 2002

(54) AGLAONEMA PLANT NAMED '000-G2'

(75) Inventor: Gregory John Mislow, III, Miami, FL (US)

(73) Assignee: Rose of Sharon, Inc., Miami, FL (US)

( * ) Notice: Subject to any disclaimer, the term of this patent is extended or adjusted under 35 U.S.C. 154(b) by 0 days.

(21) Appl. No.: 10/004,777

(22) Filed: Dec. 7, 2001

(51) Int. Cl.[7] ..... A01H 5/00

(52) U.S. Cl. ..... Plt./376

(58) Field of Search ..... Plt./376

(56) References Cited

U.S. PATENT DOCUMENTS

PP7,633 P * 8/1991 Frazer ..... Plt./88

* cited by examiner

*Primary Examiner*—Bruce R. Campell
*Assistant Examiner*—Anne Marie Grünberg
(74) *Attorney, Agent, or Firm*—C. A. Whealy

(57) ABSTRACT

A distinct cultivar of Aglaonema plant named '000-G2', characterized by its mostly upright and somewhat outwardly arching growth habit; freely clumping habit, full and dense plants; long lanceolate leaves with acuminate apices; glossy tri-colored leaves with alternating chevrons of light and medium green with random dark green spots, midveins and margins; dark green-colored leaf petioles; and low temperature tolerance.

1 Drawing Sheet

BOTANICAL CLASSIFICATION/CULTIVAR DENOMINATION

*Aglaonema hybrida* cultivar 000-G2.

BACKGROUND OF THE INVENTION

The present Invention relates to a new and distinct cultivar of Aglaonema plant, botanically known as *Aglaonema hybrida* and hereinafter referred to by the name '000-G2'.

The new Aglaonema is the result of a planned breeding program conducted by the Inventor in Miami, Fla. The objective of the breeding program is to create new Aglaonema cultivars with unique leaf variegation patterns and interesting leaf shapes.

The new Aglaonema originated from a cross made by the Inventor in March, 1997 of the *Aglaonema hybrida* cultivar Gabrielle, not patented, as the female, or seed, parent with the *Aglaonema hybrida* cultivar Maria, not patented, as the male, or pollen, parent. The new Aglaonema was discovered and selected by the Inventor in October, 1997 as a single plant within the progeny of the stated cross in a controlled environment in Miami, Fla. The new Aglaonema was selected on the basis of its unique leaf variegation pattern.

Asexual propagation of the new cultivar by cuttings since November, 1998 in a controlled environment in Miami, Fla., has shown that the unique features of this new Aglaonema are stable and reproduced true to type in successive generations.

SUMMARY OF THE INVENTION

The following traits have been repeatedly observed and are determined to be the unique characteristics of '000-G2'. These characteristics in combination distinguish '000-G2' as a new and distinct cultivar:

1. Mostly upright and somewhat outwardly arching growth habit.

2. Freely clumping habit, full and dense plants.

3. Long lanceolate leaves with acuminate apices.

4. Glossy tri-colored leaves with alternating chevrons of light and medium green with random dark green spots; dark green midveins and margins.

5. Mostly dark green-colored leaf petioles.

6. Low temperature tolerant.

In side-by-side comparisons conducted by the Inventor in Miami, Fla., plants of the new Aglaonema differed from plants of the female parent, the *Aglaonema hybrida* cultivar Gabrielle, in the following characteristics:

1. Plants of the new Aglaonema had smaller leaves than plants of the cultivar Gabrielle.

2. Leaves of plants of the new Aglaonema and the cultivar Gabrielle differed in leaf variegation pattern and coloration.

3. Plants of the new Aglaonema had darker green leaf petioles than plants of the cultivar Gabrielle.

In side-by-side comparisons conducted by the Inventor in Miami, Fla, plants of the new Aglaonema differed from plants of the male parent, the *Aglaonema hybrida* cultivar Maria, in the following characteristics:

1. Plants of the new Aglaonema had darker green leaf petioles than plants of the cultivar Maria.

2. Leaves of plants of the new Aglaonema and the cultivar Maria differed in leaf variegation pattern and coloration.

Compared to plants of the Aglaonema cultivar 000-D1, U.S. Plant Patent filed concurrently with this application, plants of the new Aglaonema are taller, more upright, have larger leaves, and differ in leaf and petiole coloration. Compared to plants of the Aglaonema cultivar 000-D2, U.S. Plant Patent filed concurrently with this application, plants of the new Aglaonema are more outwardly spreading and differ in leaf and petiole coloration.

Plants of the new Aglaonema can be compared to plants of the Aglaonema cultivar Royal Ripple, disclosed in U.S. Plant Pat. No. 9,070. In side-by-side comparisons conducted by the Inventor in Miami, Fla., plants of the new Aglaonema differed from plants of the Aglaonema cultivar Royal Ripple primarily in leaf pattern and coloration.

BRIEF DESCRIPTION OF THE PHOTOGRAPHS

The accompanying colored photographs illustrate the overall appearance of the new Aglaonema, showing the colors as true as it is reasonably possible to obtain in colored reproductions of this type. Colors in the photographs may differ slightly from the color values cited in the detailed botanical description which accurately describe the colors of the new Aglaonema.

The photograph at the top of the sheet comprises a side perspective view of a typical plant of '000-G2'.

The photograph at the bottom of the sheet comprises a close-up view of the upper surfaces of a typical young leaf (top) and fully expanded leaf (bottom) of the new Aglaonema.

DETAILED BOTANICAL DESCRIPTION

The cultivar 000-G2 has not been observed under all possible environmental conditions. The phenotype may vary somewhat with variations in environment such as temperature and light intensity without, however, any variance in genotype.

The aforementioned photographs and following observations and measurements describe plants of the new Aglaonema that were grown in 25-cm containers, in Miami, Fla., from one spring to the next in a polyethylene-covered greenhouse with 73% polypropylene shadecloth. During the production of the plants, day temperatures averaged about 85° F. and night temperatures averaged about 75° F. Plants used for the photographs and description were about 12 months from planting. Color references are made to The Royal Horticultural Society Colour Chart except where general terms of ordinary dictionary significance are used.

Botanical classification: *Aglaonema hybrida* cultivar 000-G2.

Parentage:

*Female, or seed, parent.*—*Aglaonema hybrida* cultivar Gabrielle, not patented.

*Male, or pollen, parent.*—*Aglaonema hybrida* cultivar Maria, not patented.

Propagation:

*Type*.—By cuttings.

*Time to initiate roots*.—Summer: About 21 to 30 days at 85 to 95° F. Winter: About 30 to 45 days at 65 to 85° F.

*Time to produce a rooted plant*.—Summer: About 45 days at 85 to 95° F. Winter: About 60 to 75 days at 65 to 85° F.

*Root description*.—Thick, fibrous, fleshy, and freely-branching.

Plant description:

*Appearance*.—Erect when young, becoming upright and outwardly arching as leaves develop; inverted triangle, symmetrical. Freely clumping habit give plants a very full and dense appearance. Appropriate for 25-cm containers.

*Plant height*.—About 63 cm.

*Plant width*.—About 84 cm.

*Growth rate/vigor*.—Vigorous, relatively rapid growth rate.

*Stem color*.—147A.

*Branching habit*.—Freely clumping habit; plants typically produce about 12 offshoots per plant; full and dense plants.

*Foliage description*.—Length: About 28 cm. Width: About 10.75 cm. Shape: Lanceolate. Apex: Acuminate. Base: Cordate to oblique. Margin: Entire, undulating. Orientation: Initially upright to outwardly arching. Aspect: Undulating. Texture: Mostly smooth, slightly rugose; glabrous; thick and leathery. Veins: Slightly recessed on upper surface and prominent on lower surface. Color: Young leaves, upper surface: Alternating light and medium green chevrons; light green, closest to 147C; medium green, closest to 147B; dark green ramdom spots, closest to 147A; margins, closest to 147A; glossy. Young leaves, lower surface: 146B; glossy. Fully expanded leaves, upper surface: Alternating light and medium green chevrons; light green, closest to 147B; medium green, closest to 147A; dark green random spots, much darker than 147A; margins, much darker than 147A; glossy. Fully expanded leaves, lower surface: Closest to 147A; glossy. Venation, upper surface: Closest to 147A. Venation, lower surface: 144A to 146A. Petiole: Length: About 20.5 cm. Diameter, at leaf base: About 5 mm. Diameter, at stem attachment: About 2.3 cm. Wing length: About 15.25 cm. Wing width, at base: About 1.1 cm. Color: Slightly darker than 147A with occasionally random spots and flecking, 154D to 150D.

Inflorescence description: Inflorescence development has not been observed on plants of the new Aglaonema grown under shaded greenhouse production conditions.

Disease/pest resistance: Plants of the new Aglaonema have not been observed to be resistant to pathogens or pests common to Aglaonema.

Weather tolerance: Plants of the new Aglaonema have been observed to be tolerant to wind, rain and temperatures ranging from 48 to 100° F.

It is claimed:

1. A new and distinct cultivar of Aglaonema plant named '000-G2', as illustrated and described.

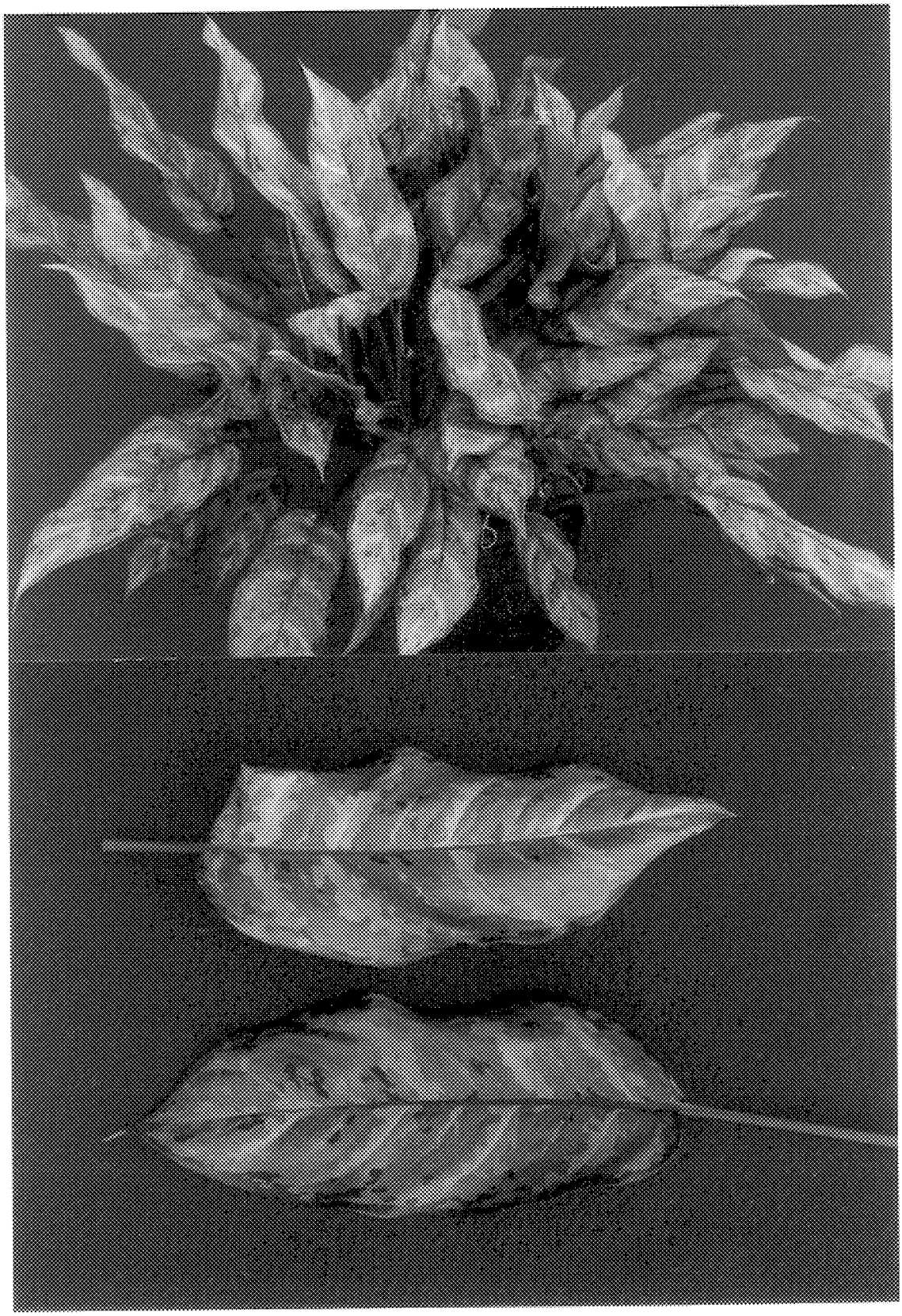

* * * * *